United States Patent [19]
Marciniak et al.

[11] Patent Number: 5,925,000
[45] Date of Patent: Jul. 20, 1999

[54] DYNAMIC BALANCE SPORT PERFORMANCE SYSTEM

[76] Inventors: Bernard Marciniak, 47 Harvard St., B 103, Charlestown, Mass. 02129; Louis A. Minafra, 293 Rider Ave., Patchogue, N.Y. 11772

[21] Appl. No.: 09/008,853

[22] Filed: Jan. 19, 1998

[51] Int. Cl.$^6$ ................................................ A61B 5/103
[52] U.S. Cl. ........................... 600/592; 600/595; 482/8; 73/172
[58] Field of Search .................... 600/592, 595; 482/8, 79, 80; 73/172

[56] References Cited

U.S. PATENT DOCUMENTS

| | | | |
|---|---|---|---|
| 2,043,187 | 6/1936 | Owens | 73/172 X |
| 2,095,268 | 10/1937 | Roberts | 600/592 X |
| 2,192,435 | 3/1940 | Downing | 73/172 |
| 2,330,317 | 9/1943 | Stewart | 73/172 |
| 3,027,761 | 4/1962 | Lauro | 73/172 |
| 4,014,398 | 3/1977 | Gresko | 600/592 |
| 4,122,840 | 10/1978 | Tsuchiya | 600/592 |
| 4,917,105 | 4/1990 | Tiiltola | 600/592 |
| 4,993,429 | 2/1991 | Krinsky | 600/592 |
| 5,049,079 | 9/1991 | Furtado | 434/253 |
| 5,341,819 | 8/1994 | Hyvarinen | 600/592 |
| 5,390,680 | 2/1995 | Brenner | 600/592 |
| 5,800,364 | 9/1998 | Glennie | 600/592 |
| 5,813,142 | 9/1998 | Demon | 600/592 X |

Primary Examiner—Michael A. Brown
Assistant Examiner—William LaMarca
Attorney, Agent, or Firm—Robert K. Tendler

[57] ABSTRACT

A dynamic balance sport performance system is provided for the dynamic testing of an individual so as to be able to provide appropriately configured shims to be placed adjacent the individual's foot in a shoe for the purpose enabling the individual to perform better in whatever sport he/she is participating. In one embodiment, an automatic system is provided for simulating shim insertion in a shoe in which two footbeds spaced apart by a predetermined distance are provided with a quadrature arrangement of hinged shim plates which are individually adjustable to predetermined shim angles. After one of the individual plates has been set, with the individual seeking to maintain his/her elbow in a horizontal position, pressure is applied to the individual's elbow until such time as a load sensor senses a predetermined load indicating that a predetermined pressure has been applied to the elbow of the individual. At this point, the individual is queried as to whether or not he/she feels more comfortable in balancing the force on the elbow using his/her entire body. The test is redone with the shim plate being actuated to different angles until such time as the individual reports that at a given load level he/she feels more comfortable. At this point, the appropriate shim angle is indicated. In one embodiment, the shim is placeable at the inner and outer side of the foot at the toe and the heel for a possible series of four shims to optimally provide balance for the individual such that when participating in athletic activities, the individual can give an optimal performance due to the dynamic balancing.

10 Claims, 11 Drawing Sheets

DYNAMIC BALANCE SPORT PERFORMANCE SYSTEM

FIELD OF INVENTION

This invention relates apparatus for the testing of initial balance leading to dynamic performance balance of an athlete and more particularly to a system for selecting shims to be placed in a shoe to improve athletic performance.

BACKGROUND OF THE INVENTION

Athletes, for whatever reason, have athletic prowess, which is both innate and is tied to what is referred to herein as dynamic performance balance. Assuming that an athlete stands on his/her feet when performing the athletic activity, it has been shown that by proper configuration of an athletic shoe to give support to the foot, and thus to the rest of the body, athletic performance can be enhanced.

Several theories surround the enhancement of athletic performance. One dynamic balance theory states that the athlete's performance will be improved if the athlete can, in some sense, provide a balanced effort when participating in the athletic activity. Athletes who can benefit from a shimming of athletic shoes to provide such balance include golfers, skiers, runners, basketball, baseball, and football players, or in fact any athlete who requires athletic shoes.

In dynamic balance the theoretical principle is that every athlete when making a movement, such as a swing of a bat or a hockey stick, will first use the muscles to put his/her skeleton in balance prior to the athletic activity. In a book by John Thie, entitled *Touch for Health,* muscle testing is discussed in which downward pressure is placed on an outstretched hand while counter pressure is placed on an opposite shoulder. In this test, guidance can be obtained on whether a particular function is out of balance energy-wise. One muscle, the deltoid muscle in the shoulder, is identified as an indicator muscle. While biofeedback is used to determine so-called "energy balance", the use of an energy balance technique as relating to footgear is not described.

SUMMARY OF THE INVENTION

In the subject invention shims or other types of spacing devices are placed within footwear to balance the athlete, thus to improve performance when the athlete is engaged in the athletic activity. It has been found that an athlete can ascertain the proper shim thickness even when the shim is only a few mils in thickness, such as the thickness of a sheet of paper, when a balancing test is performed. This balancing test involves pushing down on the outstretched elbow and rather than pushing on an opposing shoulder, the entire body is used to balance the force on the elbow. Differently shaped shims are placed under a foot and when in balance, the athlete reports significantly less effort in maintaining his/her elbow up against the downward force.

With balance appropriately adjusted for the athlete by virtue of his/her footwear having the correct shims, the athlete can perform optimally, whether this optimal performance means reduction in reaction time, increase in speed, decrease in exhaustion, or any other type of measure of athletic ability. For instance, skating ability can increase, hockey stick handling improves and shooting is more accurate. For baseball players, proper shimming of shoes can improve reaction times, pitching accuracy for pitchers, batting performance, and, in general, eye-hand coordination.

As to skiing, balance is essential in slalom events as well as ski jumping, whereas in golf, the golfer's stand is critically dependent upon proper balance. As far as tennis is concerned, proper balance improves speed over the court, reaction time, and, in general, the placing of shots in terms of accuracy and consistency.

As part of the subject invention, a system is provided for identifying the proper shims using the above test for balance. This system provides quantification to establish the correspondence between the results of balance testing and shim configuration.

While in the past there have been many insoles and shims for improving athletic performance, the prediction on an individual basis for the type and configuration of shims has been a hit or miss proposition at best.

More particularly, in the subject invention, a system is provided for analyzing each individual to determine his/her center of balance and to provide one or more appropriate shims for the footwear of the individual. In one embodiment, this is accomplished through the provision of a machine which divides each foot bed into four quadrants to provide hinged shim simulating plates. The angles of these plates correspond to the angles of the shims to be placed in the shoes. The shim plates are automatically positioned in response to an input such that the individual when standing on the plates can provide information as to whether or not the ability to maintain his/her elbow horizontally is easier.

In one embodiment, the test is to initially set the angle of one of the quadrature plates and provide a downward pressure on the individual's elbow with the elbow extended laterally. This pressure is measured by a load sensor for quantification purposes and when a predetermined pressure is exerted, a threshold detector provides an indication that the appropriate force has been exerted. This predetermined amount of force is that force necessary to counteract the pressure down on the individual's elbow, which is the result of the individual's muscles and body reacting against the force.

Since the individual is standing on the quadrature plates, and with at least one of the quadrature plates simulating shims in the footwear, when the individual reports that it is significantly easier to resist the force, the shim is at the appropriate angles.

In one embodiment, the quadrature plates are hinged along the longitudinal center line to the foot bed so as to be able to adjust each of the four plates at an angle varying from 0° to 15° for the inner side of the foot and the outer side of the foot, both at the toe and at the heel. Thus, in one embodiment, there are four adjustments which can be made in terms of shimming, either the toe or the heel of the individual at its inner or outer side.

In order to provide precise measurements, in one embodiment, two footbeds are spaced apart by a distance, D, which is settable. With the individual standing on the spaced apart footbeds, the distance between the footbeds is adjusted so that a predetermined stance which is comfortable to the individual is set.

At least one of the hinged shim plates making up the foot bed is then adjusted in a predetermined manner which is settable by the individual doing the testing.

Thereafter, the individual is asked to extend his/her elbows laterally with pressure being applied to one of the elbows by any means such as the hand of a testing instructor, such that a downward force is placed on one of the elbows. The individual is told to resist the force in order to maintain the elbow in a lateral position.

After an initial test with initial setting for the shim plate, the shim plate is adjusted to another position and the same test is redone, with the individual reporting either that it is easier or less easy to maintain his/her elbow in a horizontal orientation for a given pressure. The act of resisting the force on the elbow causes the muscles in the body to react against the shim plate.

It has been found that at a certain shim plate angle for the toe and/or the heel, the amount of effort necessary to maintain the elbow horizontal is significantly decreased, indicating an optimal setting of the shim angle.

From this information, a shim can be selected for the particular individual to improve the individual's athletic performance. In one embodiment, a shim is inserted into a slot within the footwear for convenience. Alternatively, the shim can be inserted between the inner liner of the athletic shoe and the sole from the top of the shoe.

While quadrature shim plates have been described in terms of providing a platform for the individual in order to measure dynamic balance, the hinge plate embodiment may be supplanted by other means such as inflatable shims, automatic fixed shim insertion and other types of tilt apparatus.

In summary, a dynamic balance sport performance system is provided for the dynamic testing of an individual so as to be able to provide appropriately configured shims to be placed adjacent the individual's foot in a shoe for the purpose enabling the individual to perform better in whatever sport he/she is participating. In one embodiment, an automatic system is provided for simulating shim insertion in a shoe in which two footbeds spaced apart by a predetermined distance are provided with a quadrature arrangement of hinged shim plates which are individually adjustable to predetermined shim angles. After one of the individual plates has been set, with the individual seeking to maintain his/her elbow in a horizontal position, pressure is applied to the individual's elbow until such time as a load sensor senses a predetermined load indicating that a predetermined pressure has been applied to the elbow of the individual. At this point, the individual is queried as to whether or not he/she feels more comfortable in balancing the force on the elbow using his/her entire body. The test is redone with the shim plate being actuated to different angles until such time as the individual reports that at a given load level he/she feels more comfortable. At this point, the appropriate shim angle is indicated. In one embodiment, the shim is placeable at the inner and outer side of the foot at the toe and the heel for a possible series of four shims to optimally provide balance for the individual such that when participating in athletic activities, the individual can give an optimal performance due to the dynamic balancing.

BRIEF DESCRIPTION OF THE DRAWINGS

These and other features of the subject invention will be better understood with reference to the Detailed Description taken in conjunction with the Drawings of which.

DETAILED DESCRIPTION

Figure 1:
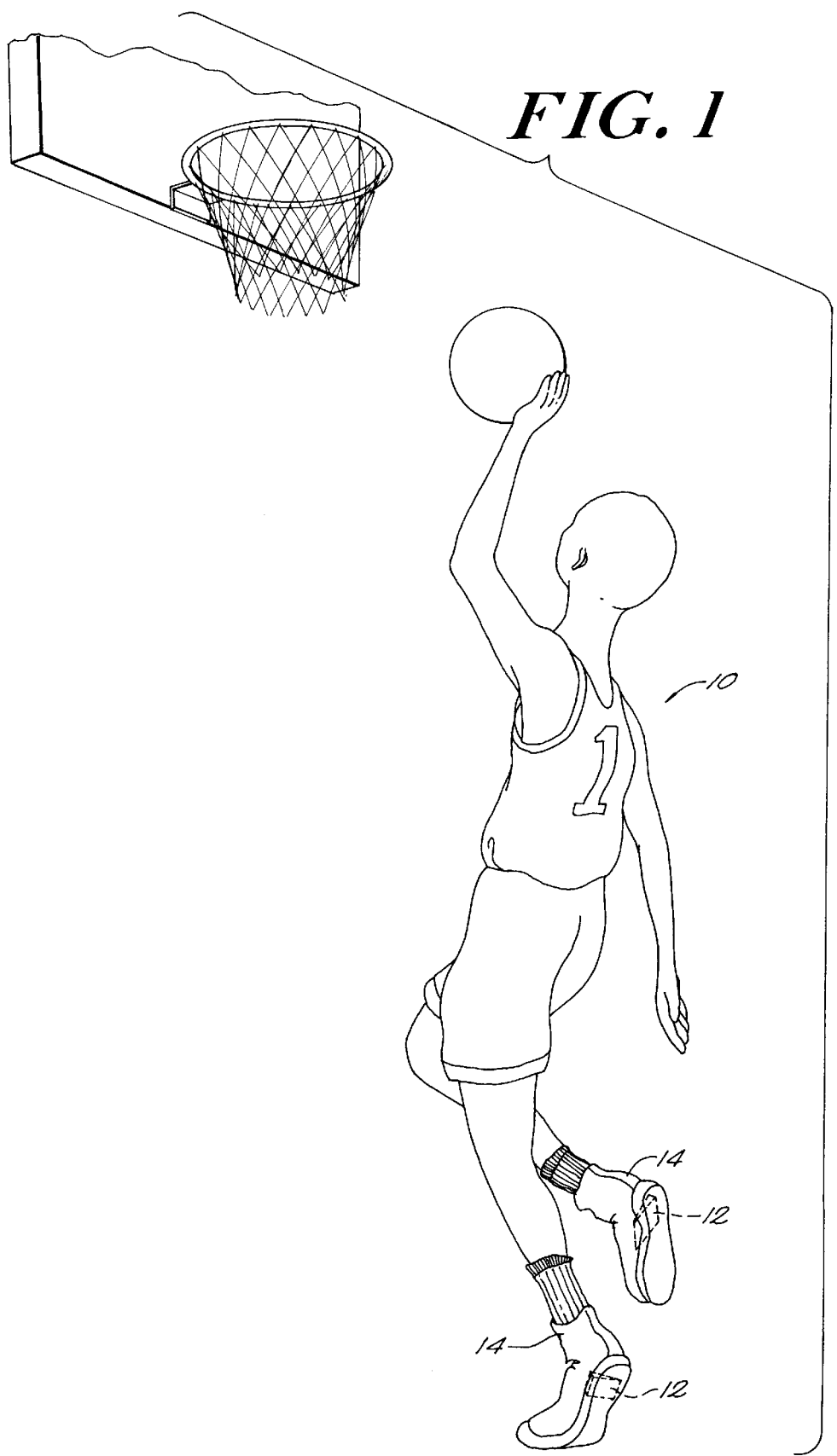
FIG. 1 is a diagrammatic illustration of a basketball player having footwear into which are inserted shimming devices for optimizing the athlete's performance.

Referring now to FIG. 1, in order to improve the performance of an individual 10, in this case illustrated as playing basketball, it has been found that if the individual's dynamic balance can be improved, his/her athletic performance will be improved. In order to accomplish this, in the subject system, shims 12 are placed in athletic footwear 14 in order to improve the individual's dynamic balance. The subject system provides apparatus that measures what shim configuration the shim should take through a dynamic testing technique in which, in one embodiment, the angle of the shim is selected as a result of the testing.

Figure 2:
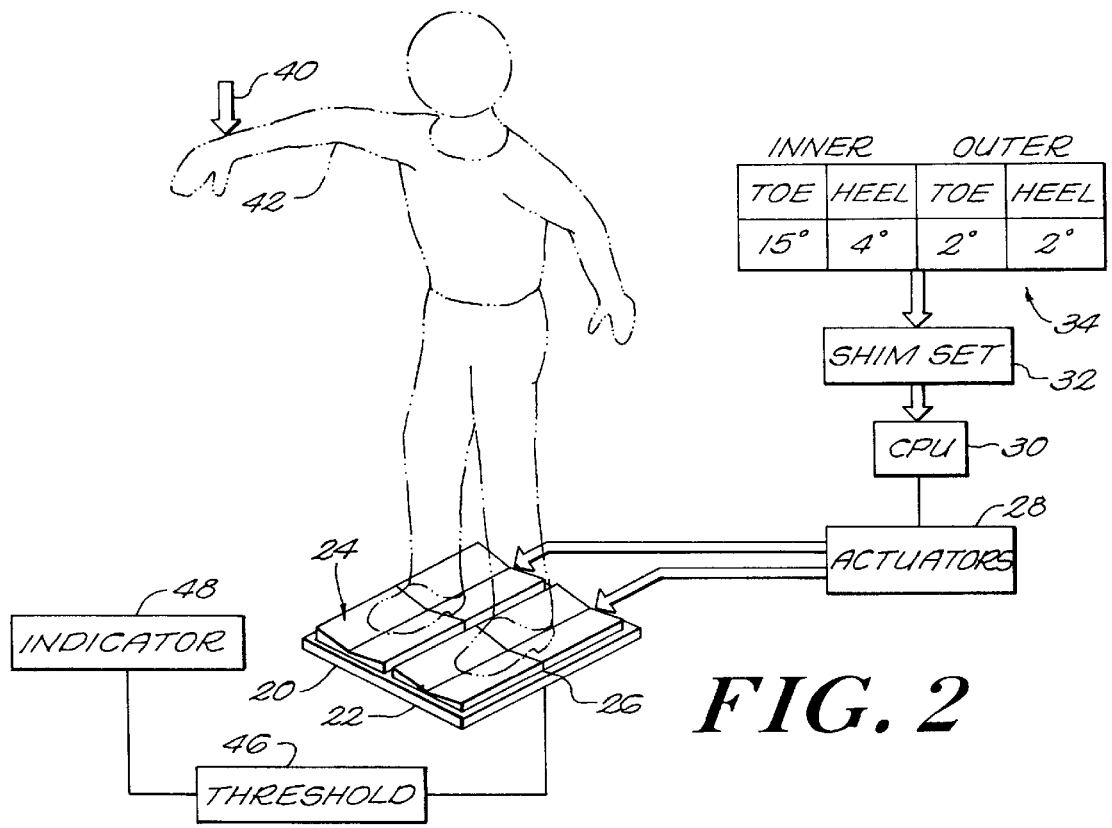
FIG. 2 is a block diagram illustrating the control of quadrature shim plates serving as footbeds for use in the dynamic balancing technique, also indicating the imposition of a force on a laterally extending elbow of an individual to provide an off-balance pressure to the body.

In one embodiment, as illustrated in FIG. 2, two separated footbeds 20 and 22 are used to support quadrature shim plates 24 and 26 respectively, with each of the shim plates being adjustable by actuators 28 under the control of a CPU 30 which sets the plates to correspond to a given shim angle. The shim angle is set via a unit 32 so that for each of the feet, the inner and outer toe and heel shims can be specified through an input device 34.

During the test, a force illustrated by arrow 40 is placed upon an arm 42 of the individual shown in dotted outline after the weight of an individual is determined and a force threshold, as illustrated at 46, which subtracts out the individual's weight is exceeded. When the threshold is exceeded, an indicator 48 indicates that a predetermined pressure has been placed on the individual's arm. Note that the force is applied to the arm or shoulder associated with the foot whose shims are to be adjusted.

In one embodiment, first one foot then the other is tested for shimming angles. For any given foot, after a series of tests when the individual reports that it is easier to maintain himself/herself upright with an off center force such as that illustrated by arrow 40 then the corresponding shim angles are those to be specified for the shim inserts to the individual's footwear. Note that a dramatic reduction in effort will occur upon the proper shim angles having been found.

First one foot is shimmed and then the other, with the same test being applied for the other foot using downward pressure on the associated arm.

Figure 3:
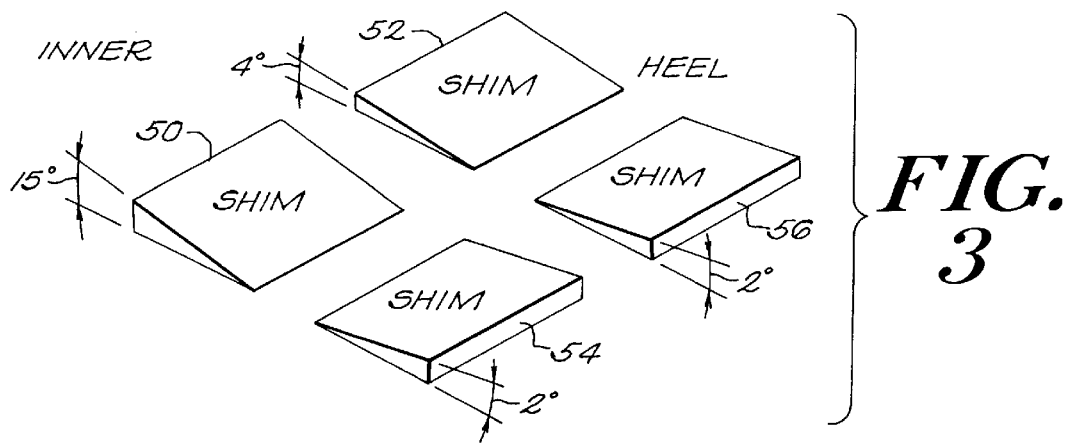
FIG. 3 is a diagrammatic illustration of various shims to be inserted into the footwear of an individual in accordance with indications from the system of FIG. 2.
Figure 4:
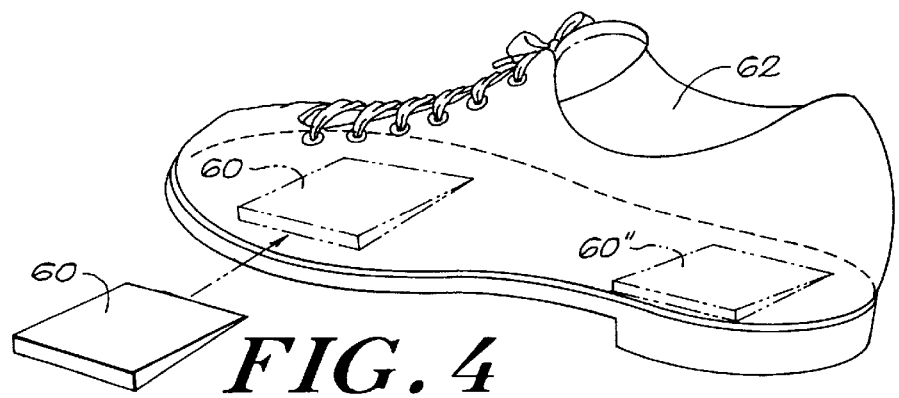
FIG. 4 is a diagrammatic illustration of an athletic shoe with pockets into which the shims illustrated in FIG. 3 are to be inserted.

Having ascertained the angles of the shim plates which the individual reports make it easier for him/her to maintain his/her body upright, shims can be fabricated with these shim angles and inserted into the individual's footwear, as illustrated in FIGS. 3 and 4.

Referring to FIG. 3, the shims can be placed at the toe or heel and at the inner or outer side of the foot. Shim angles from 0–15 degrees have proved to be useful in the apparatus shown in FIG. 2. Note that shims 50, 52, 54 and 56 correspond respectively to the inner portion of the foot of the individual at his/her toe and heel, and the outer portion of the individual's foot at the toe and the heel respectively.

As can be seen from FIG. 4, a shim 60 can be inserted into footwear 62 of an individual through the utilization of a pocket in the shoe (not shown) such that the shim can reside either at the outer toe of shoe 62 as illustrated at 60', or at the heel as illustrated at 60".

In operation of the system, the first step is to have an individual stand as comfortably and naturally as possible on a mat which has lines on it that indicate the center of the heel of the individual. When standing comfortably, the distance from a center line to each of the centers of the person's heels is measured. The measured offset is then entered into the machine as the spread distance, with the machine positioning the respective footbeds accordingly.

After the footbeds have been set at the appropriate spacing, the individual's weight is checked through the utilization of a weight sensor.

The shim angles are then obtained as follows. Starting with the individual standing on the machine, in one embodiment, first the left foot then the right foot, or vice versa, is tested. One starts with the person raising his/her elbow horizontally to the side, with the operator exerting a downward force of approximately five pounds as indicated when the force sensor senses such a force and the indicator indicates that such a force has been exerted. Note that the weight of the individual is first subtracted out so that the output of the force sensor is the force exerted on the person's arm.

The machine operator notes the angle of the arm with respect to the body and reminds the person to try to maintain his/her arm in a horizontal position. At this point, the person is asked to gauge their feeling of exertion.

The operator then raises one of the shim plates a few degrees corresponding to an increase in shim angle and repeats the test by exerting a five-pound pressure on the person's elbow and asking the person whether or not he/she feels less or more exertion with the five-pound pressure being applied.

The test procedure continues with each of the four shim plates associated with the left foot and until such time as angles are established for each of the shims. Note, in one embodiment after each test, the shim plates are returned to zero in order to test the other plates.

After each of the plates of the left foot have been specified as to shim angle, a final test is made with all of the shim plates set to previously found optional settings. Thereafter, optionally, the right foot is adjusted in the same manner with the left foot residing on the adjusted shim plates.

If a closer fit is required, each of the shims can be adjusted in a fine control setting from the points previously established, with the person reporting either a lesser or greater degree of exertion for each of the new settings.

Thereafter, a printout is made or a permanent record is kept of the shim angles so that appropriate shims for the left and right feet can be manufactured or selected.

It will be appreciated that when the left foot is adjusted, the right foot is situated on an essentially flat platform. One of two scenarios can then exist. Either the left foot plates are adjusted to 0° and the right foot adjusted; or, as described above, the left foot plates are maintained at previously found optimal angles and the right foot then adjusted.

What is accomplished through the utilization of this technique is the provision of shims which place the body in dynamic balance. It is noted that there is a definite point at which when the shims are adjusted, the effort to maintain one's body erect upon a downward deflection of one's upper limb is dramatically reduced. This dramatic reduction in effort reflects an in-balance condition of the individual.

One plausible explanation of the reason why athletic performance is improved is that when an individual is performing an athletic feat or simply exercising, the mind is in an overloaded condition to control the individual's muscles to perform the athletic task at hand. However, in addition to performing the athletic task, the brain must take into account such things as wobbling and elemental balance. Keeping the body in a dynamically balanced position requires mental control, which is super-imposed upon the mental activity to control the hundreds of thousands of muscles to do the athletic chore.

By removing the balance portion of the mental activity for muscle control, athletic performance can be enhanced since that portion of the brain utilized to control the athletic activity is now directed to the particular athletic activity without being diverted to balance maintaining functions.

Figure 5:
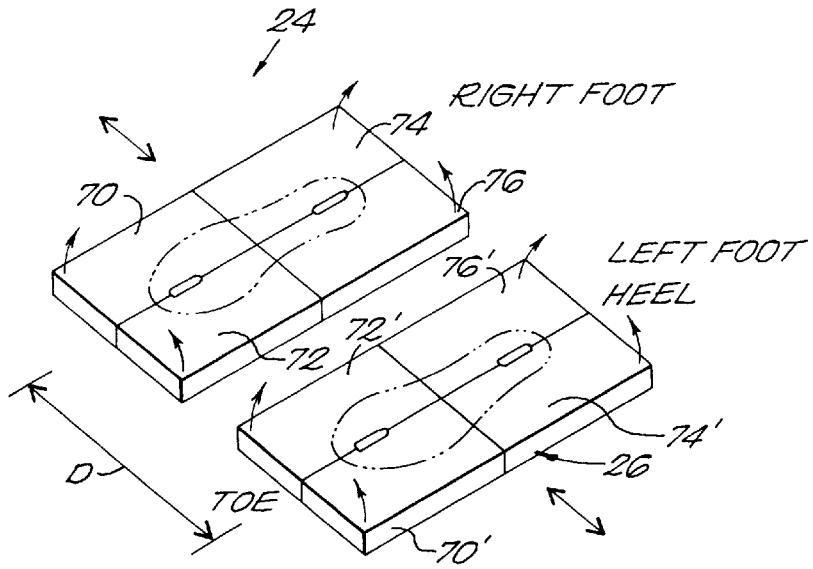
FIG. 5 is a diagrammatic illustration of the quadrature shim plates utilized in the two separated footbeds in the system of FIG. 2, showing the pivoting of each of the shim plates around a longitudinally extending centerline as well as control of foot bed separation.

Referring now to FIG. 5, shim plates 24 and 26 respectively of the right foot and left foot are illustrated pivoted at hinges 25. Here, each of the footbeds includes a quadrature arrangement of shim plates, such that for the right foot there are toe shim plates 70 and 72 corresponding respectively to the outer and inner position of the foot; whereas outer and inner heel plates 74 and 76 control the shim plates for the heel of the right foot. Similarly, for the left foot, plates 70' and 72' control respectively the outer and inner toe shim positions; whereas plates 74' and 76' control the outer and inner heel shim positions for the left foot.

Figure 6:
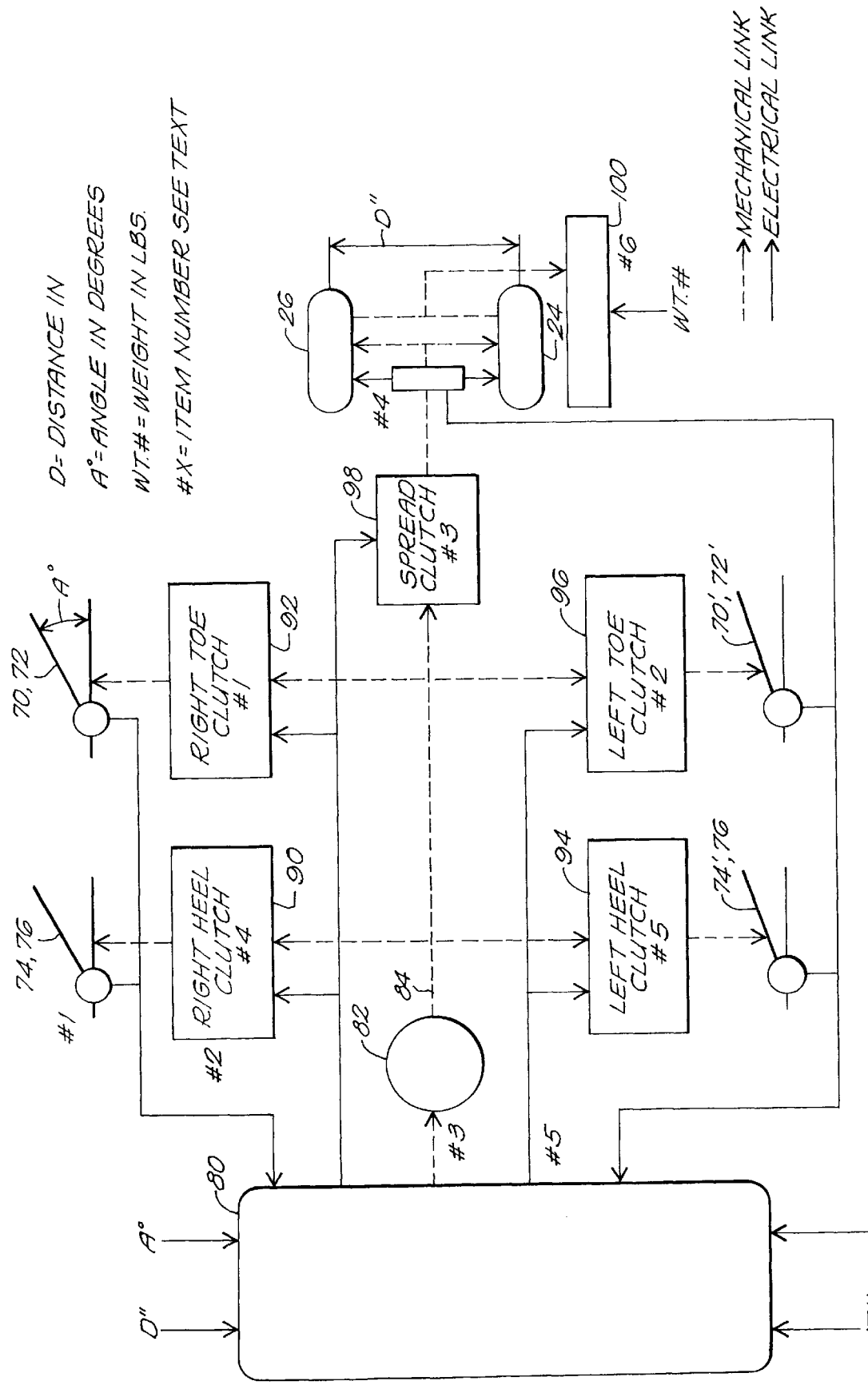
FIG. 6 is a diagrammatic illustration of the control of actuators for moving the quadrature shim plates of FIG. 5 through the utilization of computer generated instructions, also showing the ability to automatically set the distance between the separated footbeds.

Referring now to FIG. 6, a system for positioning the shim plates is illustrated. Here a CPU 80 is used to control a motor 82 and a number of clutches which connect the mechanical output of motor 82 to drive, in this embodiment, the right heel shim plates 74 and 76, the right toe shim plates 70 and 72, the left heel shim plates 74' and 76' and the left toe shim plates 70' and 72'. It will be noted that respective clutches 90, 92, 94 and 96 are utilized to connect power from motor 82 to position the associated shim plates.

As will be discussed in connection with FIGS. 9–17, in one embodiment it has been found that only the inner side or the outer side of a foot needs to be provided with shims in order to provide for the appropriate correction. This takes into account two general conditions where the feet are either inwardly or outwardly canted, called supernatant or pronatant. While the subject system will be described in connection with adjusting only inner or outer shim plates for a given foot, it will be appreciated that independent control can be provided to provide shim angles for any of the four shim plates to provide maximum control over the shimming process.

Additionally, motor 82 is utilized to drive a spread clutch 98 which transfers mechanical power from motor 82 to control the separation between footbeds 24 and 26. This controls the distance, D, between the centers of these footbeds, with this distance being established by a comfortable stance of the individual prior to getting on the machine.

Note also that a force sensor 100 senses the weight of the individual as he/she stands balanced on footbeds 24 and 26, thus to be able to subtract out the weight of the individual from a force measurement reflecting the force on one of the individual's outstretched arms.

Figure 7:
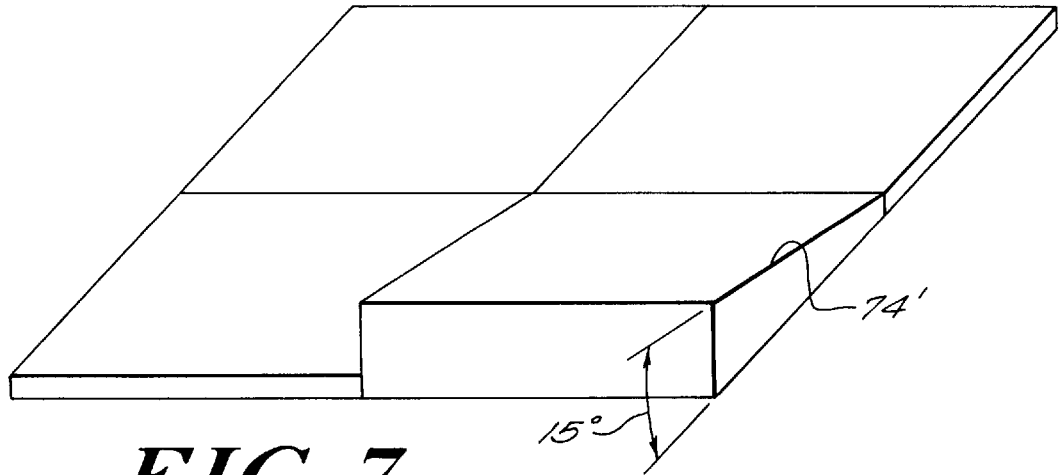
FIG. 7 is a diagrammatic illustration of the elevation of one of the shim plates of FIG. 5 at the left outer heel, illustrating the angle at which the shim plate can be adjusted, for instance, to 15 degrees.

Referring now to FIG. 7, it will be appreciated that what is shown is the raising of the shim plate associated with the outer portion of the individual's left foot at his/her heel. This is shim plate 74' of FIG. 5. It will be appreciated that by experimentation, any angle between 0 and approximately 15 degrees is useful in obtaining dynamic balance.

Figure 8:
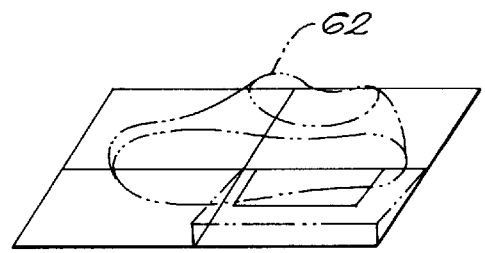
FIG. 8 is a diagrammatic illustration of a shim having a shim angle corresponding to the shim angle of the shim plates of FIG. 7 inserted into a shoe for raising the outer heel to promote optimal athletic performance.

Referring now to FIG. 8, it is this shim at 15 degrees which is inserted at the left heel of the footgear 62 of FIG. 4, with it having been ascertained that this particular shim is appropriate to promote the dynamic balance of the individual.

Figure 9:
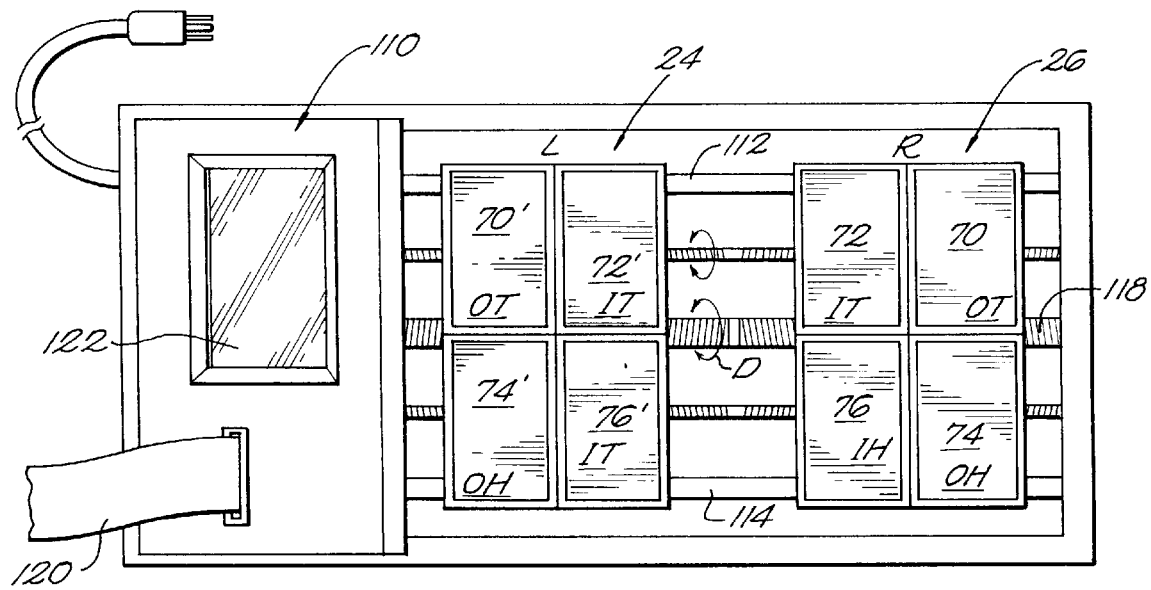
FIG. 9 is a top view of one embodiment of the subject invention showing the CPU and display/printer mounted to the side of the footbeds of FIG. 5 with a worm gear drive to control the separation of the footbeds.

Referring now to FIG. 9, a top view of such a machine is illustrated in which a control unit 110 is generally indicated to be to the left of the machine which houses the aforementioned motor and clutching apparatus and is connected to footbeds 24 and 26 which rest on rails 112 and 114. Spacing between footbeds 24 and 26 is adjusted through an acme screw drive 118, such that the separation between the footbeds can be readily controlled.

Each of the footbeds 24 and 26 have four shim plates which correspond to those illustrated in FIG. 5.

Unit 110 has an internal printer (not shown) providing a printout 120 of the settings of the shim plates. Note that display 122 displays to the operator and to the individual the status of the machine, the shim plate angles and other necessary data.

Figure 10:
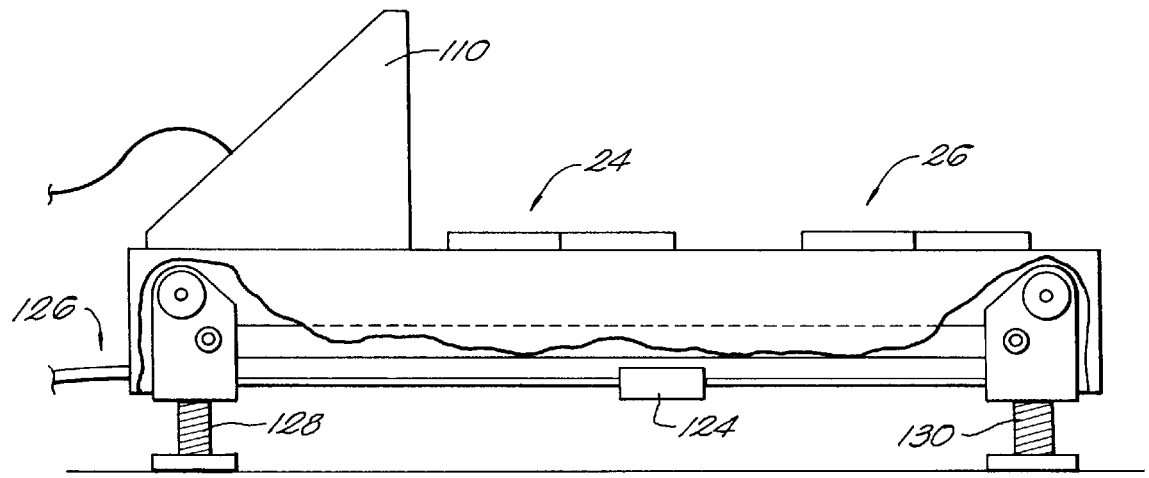
FIG. 10 is a side view of the apparatus of FIG. 9 illustrating the utilization of a load cell under the apparatus of FIG. 9 showing the adjustability of the load cell so as to center the load cell underneath the individual.

The machine at FIG. 9 is shown in side view in FIG. 10 in which a load cell 124 is positioned beneath footbeds 24 and 26 to ascertain the weight of an individual and thereafter the pressure exerted downwardly on the individual's arm during the testing. Note that frame 126 on which footbeds 24 and 26 are mounted can be leveled by adjustable feet 128 and 130 as illustrated.

Figure 11:
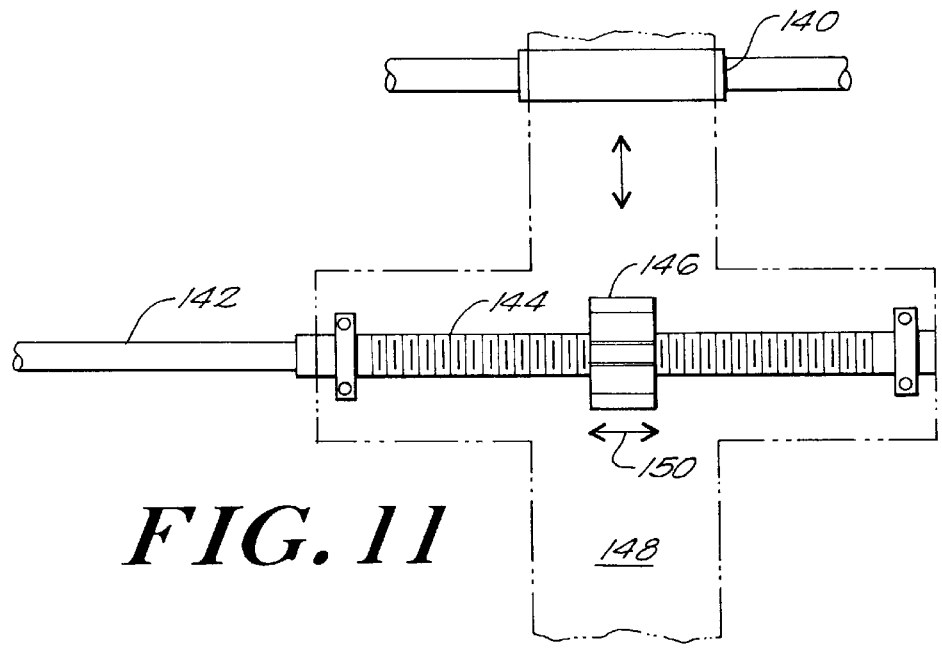
FIG. 11 is a top view of a portion of the foot bed base with an upper slide bearing supporting the base so it can be moved to spread the two footbeds apart, also showing a cam lifter roller assembly and associated lead screw.

Referring now to FIG. 11, prior to describing the mechanical adjustment to the shim plates, it will be appreciated that a slide bearing 140 is provided to permit sliding of the footbeds so as to accomplish the required initial spacing between them.

Figure 12:
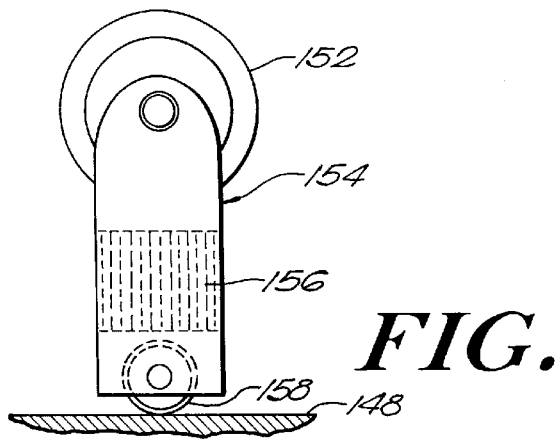
FIG. 12 is a side view of a cam lifter roller assembly used as part of an actuator for the tilting of the shim plates of FIG. 5.

With respect to the adjustment of the shim plates, in one embodiment, a shaft 142 a having a screw drive 144 is used to position a roller assembly 146 above a plate 148. The roller assembly moves in the direction of double-ended arrow 150, and as illustrated in FIG. 12 includes a rotary cam 152 in the shape of a wheel mounted to a housing 154 which has a threaded channel 156 to accommodate the passage of screw drive 144 therethrough. A wheel 158 is located at the bottom of housing 154 to rest on surface 148 that permits lateral movement of the assembly.

Figure 13:
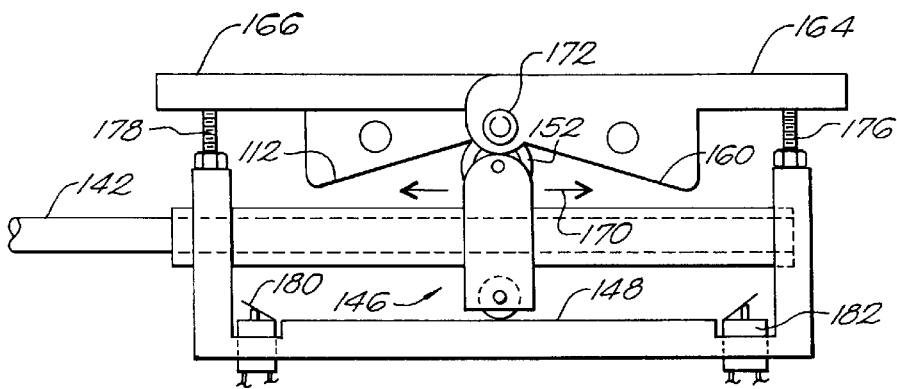
FIG. 13 is a side view of one embodiment of the actuator of FIG. 12 utilizing the cam lifter roller assembly of FIG. 12 and a cam follower surface on each of the plates, such that the plates can be raised and lowered due to the coaction of the roller bearing on the surface on the cam follower underneath one of the shim plates.

Referring now to FIG. 13, it can be seen that movement of assembly 146 provides that the wheel-shaped cam 152 coact with a cam following surface 160 or 162 on respective shim plates, here illustrated at 164 and 166 respectively.

With assembly 146 driven in the right direction as illustrated by arrow 170, because shim plate 164 is pivoted at 172 it moves upwardly in accordance with the coaction with the cam and cam follower as the assemblies move to the right.

When the assembly is moved to the left, shim plate 166 is moved upwardly in accordance with the coaction of cam 152 with cam following surface 162. Note that stops 176 and 178 are provided to limit the downward movement of the respective shim plate such that when, for instance, the interior shims are to be moved the exterior shims are in a horizontal position as limited by the appropriate stop. As can be seen, the movement of assembly 146 can be controlled through limit switches 180 and 182 to prevent overrunning during operation.

Figure 14:
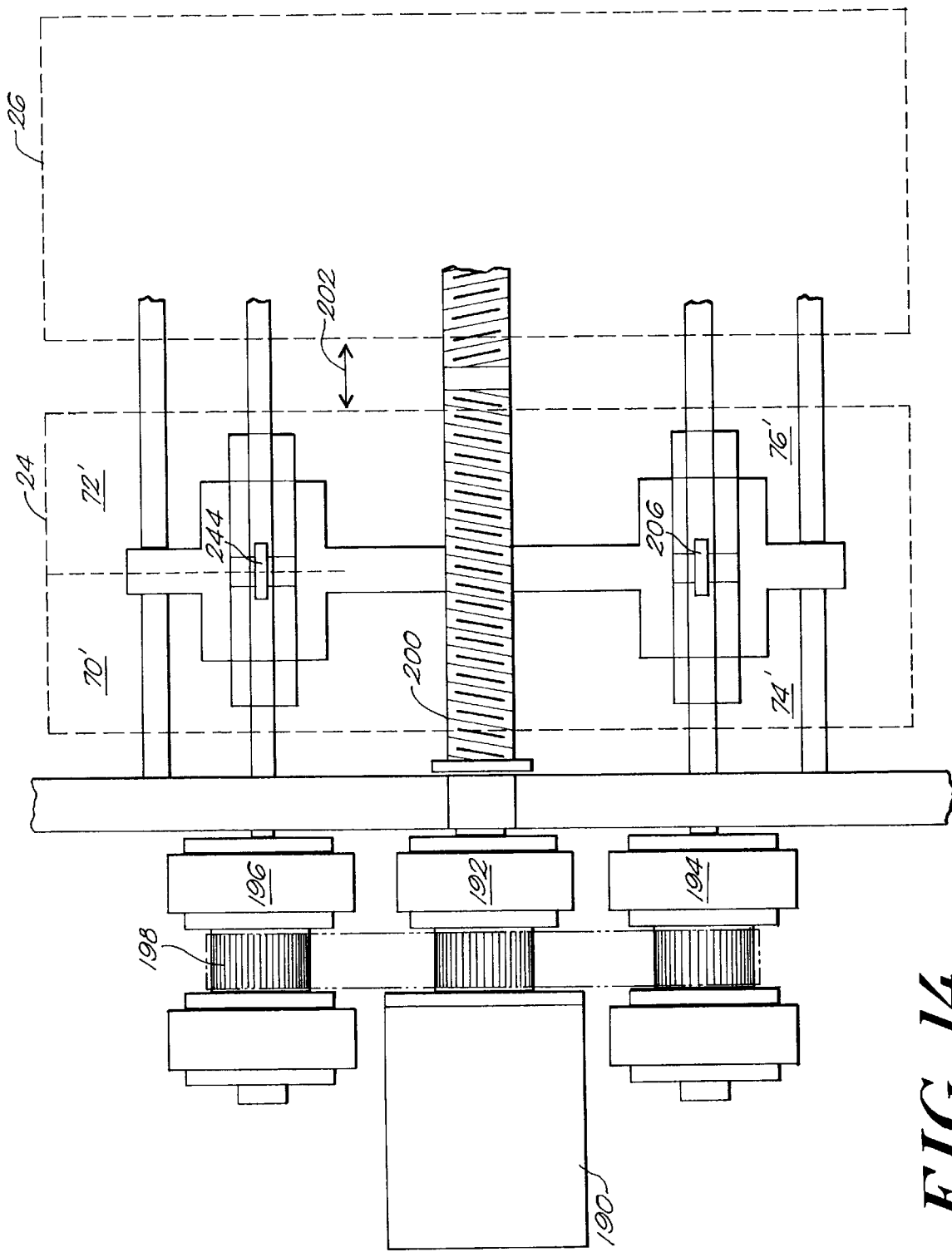
FIG. 14 is a top view of motor and clutch assembly of FIG. 9 illustrating a single motor drive to adjust shim angles and foot bed separation through the use of clutches.

Referring now to FIG. 14, a motor 190 is disposed within unit 110. The output shaft of motor 190 is coupled to clutches 192, 194 and 196 through the utilization of a single belt 198, with clutch 192 coupled to acme drive screw 200 which is utilized to position respective footbeds 24 and 26 as illustrated by double-ended arrow 202.

Likewise, clutch 196 is utilized to control cam 204, the movement of which positions the outer and inner shim plates 70' and 72' for the left foot.

Likewise, clutch 194 controls the movement of cam 206 to control respectively outer and inner shim plates 74' and 76' for the right foot.

It will be appreciated that similar coupling can be utilized to control the associated cams under the shim plates of foot bed 26.

Figure 15A:
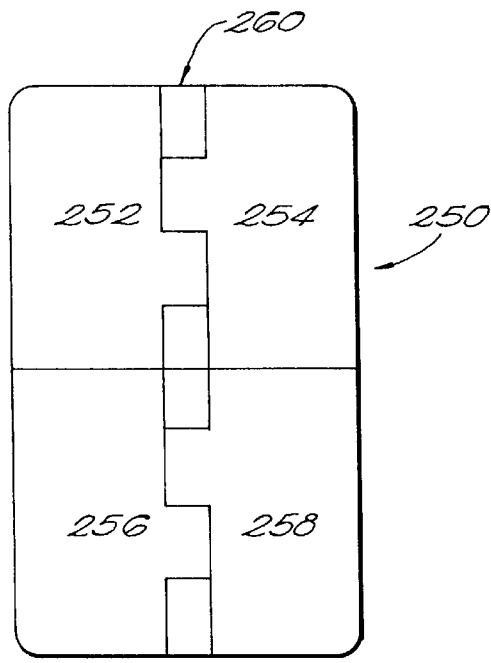
FIG. 15A is a top view of a quadrature shim plate of FIG. 9 illustrating the hinge structure therefor.
Figure 15B:
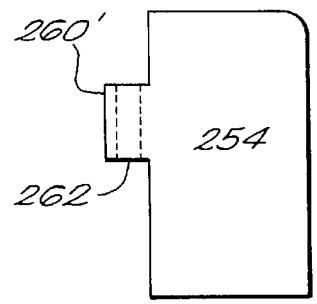
FIG. 15B is a top view of one of the shim plates of FIG. 15A showing the pivot bearing therefor.

As illustrated in FIG. 15A, a quadrature shim plate assembly 250 can be provided with four shim plates 252, 254, 256 and 258. Here, quadrature shim plates are interlocking along a longitudinally running axis carrying pivot bearing 260. As illustrated in 15B, shim plate 254 has a pivot bearing 260' in the form of a tab having a central bore 262.

Figure 15C:
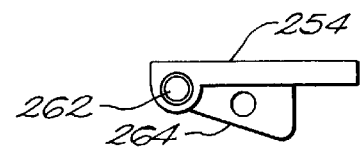
FIG. 15C is a side view of the cam follower, hinge pivot arrangement for one of the shim quadrature plates of FIG. 15A showing the pivot bearing and inclined cam follower.

A side view of this shim plate is shown in FIG. 15C, which shows bore 262 forming a pivot for shim plate 254, also showing an associated cam follower surface 264.

Figure 16:
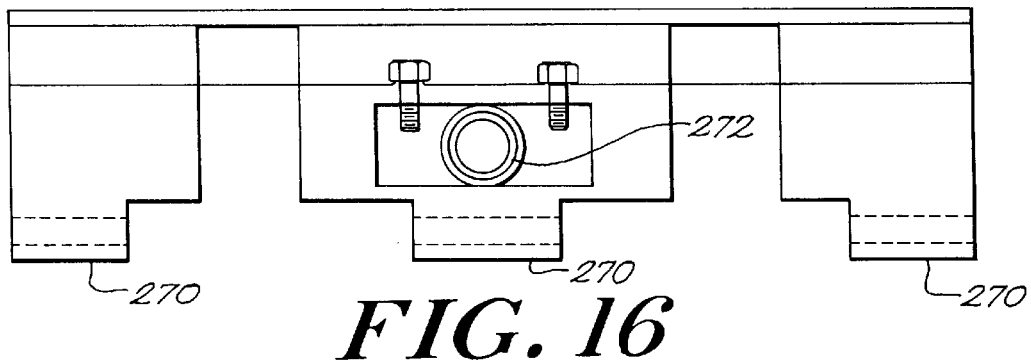
FIG. 16 is a side view of the assembly that holds the shim plates for each foot bed, also showing an acme threaded bushing at the center used to spread apart the footbeds.

Referring now to FIG. 16, the assembly that holds the shim plates is illustrated. Here, the pivot bearing for each of the shim plates is shown as having a central bored tab portion 270 which is interleaved between the tabs of the shim plates and through which a pivot pin (not shown) is passed to provide the pivoted action of the shim plates. Additionally, a threaded bore 272 receives the acme threaded lead screw to position the entire assembly.

Figure 17:
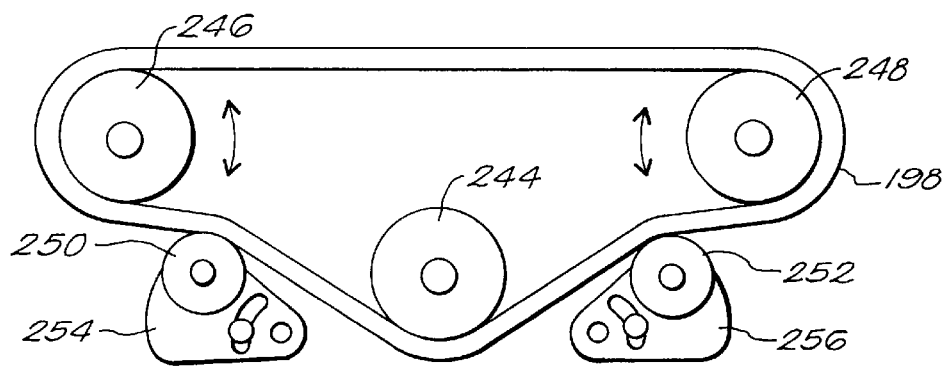
FIG. 17 is a diagrammatic illustration showing a single drive belt going around three clutch shafts, also showing two belt tightening assemblies.

Referring now to FIG. 17, motor 190 has a drive pulley 274 which contacts belt 198 that goes around pulleys 246 and 248 respectively coupled to the aforementioned clutches 194 and 196. It will be appreciated that idle rollers 250 and 252 are located on hinged assemblies 254 and 256 respectively to take up slack in the belt.

Figure 18C:
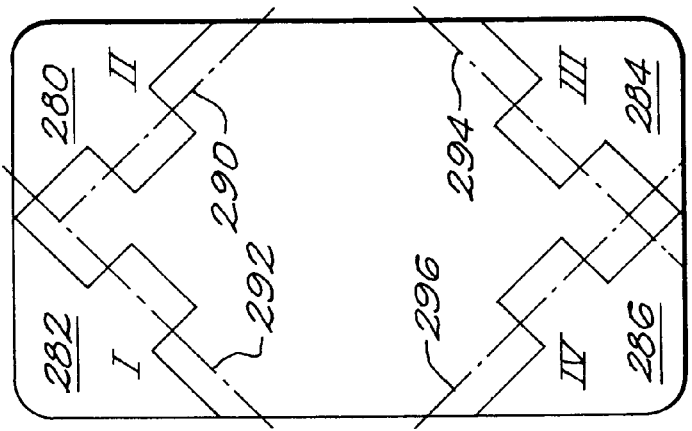
FIGS. 18A, B and C are top views of variations for the quadrature shim plates of FIG. 7, illustrating respectively a centerline hinged configuration, configuration to spread the pressure points on the foot, and a configuration in which only the tips of the shim plates are raised.
Figure 18B:
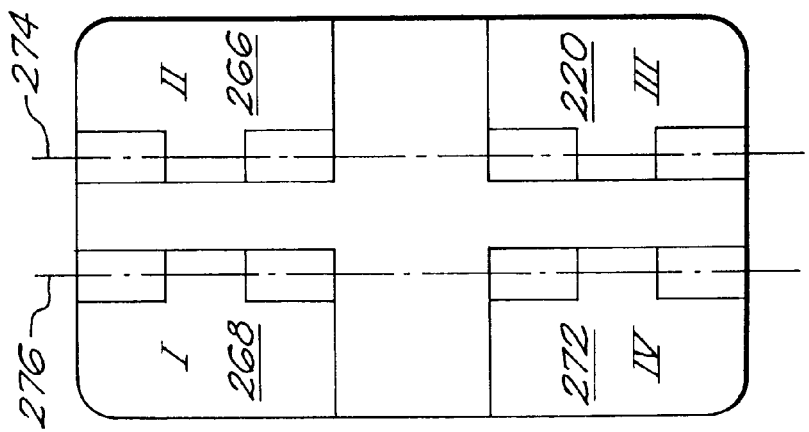
Figure 18A:
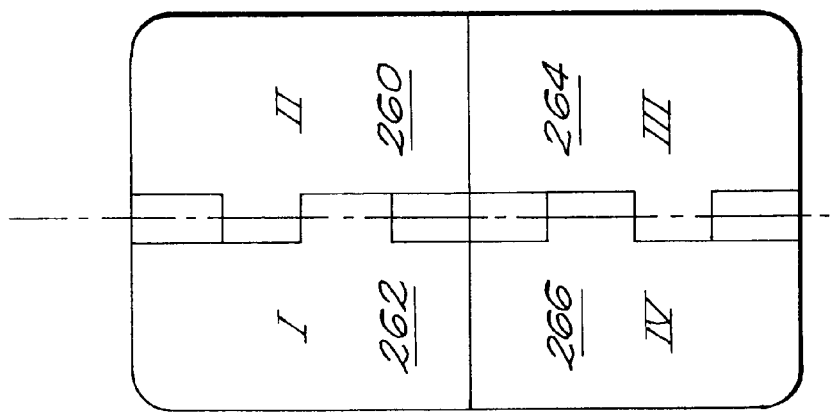

Referring now to FIG. 18A, it will be appreciated that there are several different types of configurations that the shim plates can take. Here, for instance, four levels of inner and outer adjustment are shown by plates 260, 262, 264 and 266 which control inner and outer portions of the toe and heel of the left foot. If more control is required, the outer portions of the heel and toe can be adjusted as illustrated by the spaced apart plates 266, 268, 270 and 272 having separated longitudinal hinge axes 274 and 276. If further fine tuning control at the very ends of the toes and heels is required, the shim plate assembly can be of the configuration shown in FIG. 18C in which hinge plates 280, 282, 284 and 286 are located along respective axes 290, 292, 294 and 296.

It will be appreciated that the configuration of the hinge plates can offer gross or fine tuning for various portions of the foot to provide the required balance.

Figure 19A:
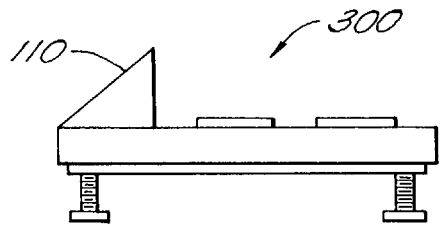
FIGS. 19A, B and C are diagrammatic illustrations of three different display options to display the results of the testing done by the subject system, respectively unit mounted, handheld and wall mounted displays; and, FIG. 20 is a top view of a spread mat having indicia to indicate distance to the center of an individual's heel when in a relaxed stance used prior to the individual stepping on the subject machine to set the separation for the footbeds.
Figure 19B:
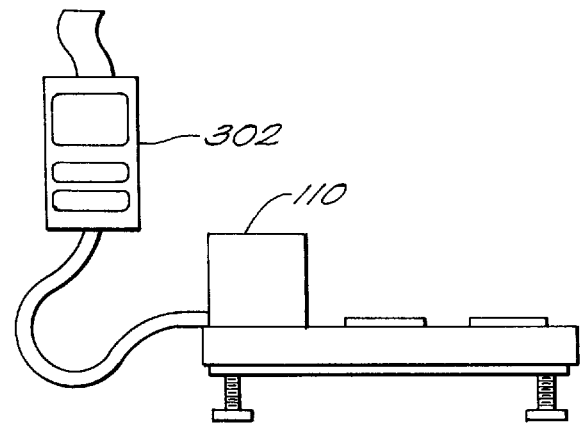
Figure 19C:
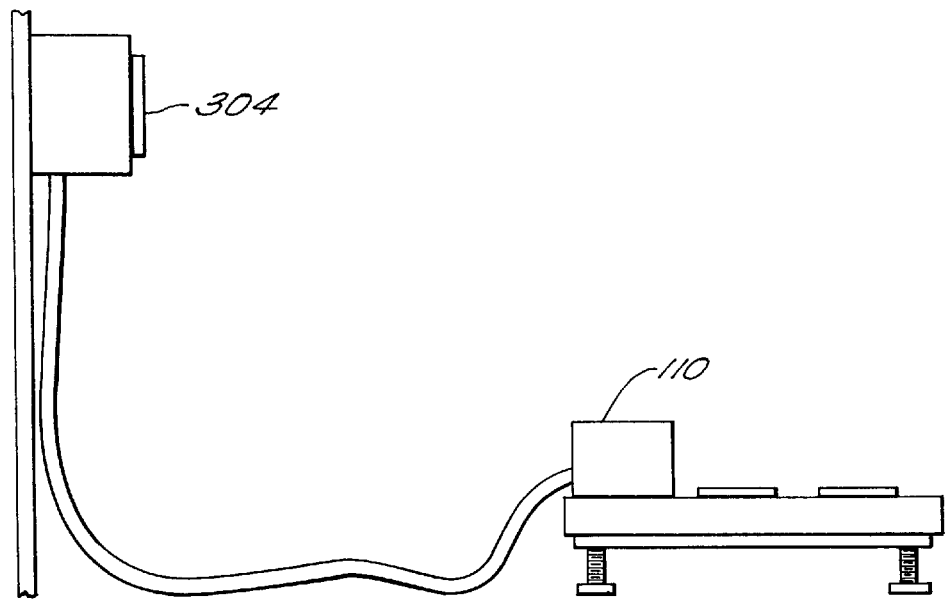

Referring now to FIG. 19 as illustrated at 300, the subject machine can have the display co-located on the frame carrying the left and right footbeds within housing 110.

Alternatively, a handheld display 302 may be provided which is coupled to unit 110 on the frame.

As illustrated at 304, a wall-mounted display can be provided coupled to unit 110, all for the convenience of the operator performing the balancing operation.

Figure 20:
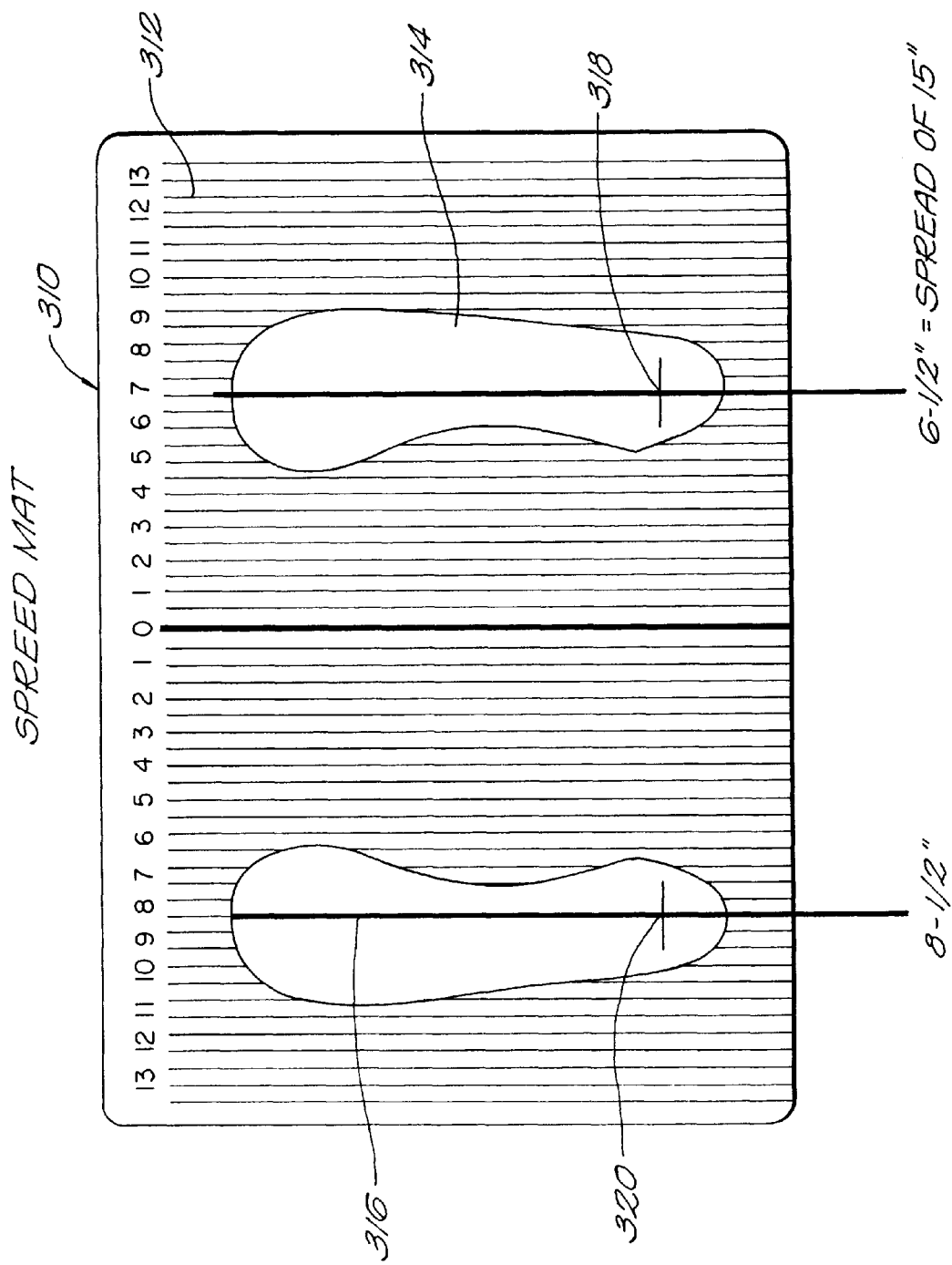

Referring now to FIG. 20, a spread mat 310 may be provided to initially measure the spread required for separation of footbeds 24 and 26. Here a ruled surface generally indicated at 312 is used as a mat on which the individual stands in a balanced, relaxed manner. Moveable indicia on this mat, such as indicia 314 and 316 are used so as to be able to accurately determine the center of the heel of the right and left foot of the individual here illustrated at 318 and 320.

By ascertaining the distance between these two center marks, the distance between the footbeds can be calculated so that when the individual mounts the machine and places his/her feet on the footbeds, the stance will be a relaxed, balanced one.

Having above indicated several embodiments of the Subject Invention, it will occur to those skilled in the art that modifications and alternatives can be practiced within the spirit of the invention. It is accordingly intended to define the scope of the invention only as indicated in the following claims.

What is claimed is:

1. Apparatus for permitting dynamic balance of an individual, comprising:
   means including a positionable shim plate for establishing a foot shim configuration for a shim to be positioned at the bottom of the foot of an individual, said shim plate portion establishing means including a cam actuable to position said shim plate and a cam follower carried by said shim plate, whereby a foot shim may be configured in accordance with the position of said shim plate and may be inserted into a shoe of said individual.

2. The apparatus of claim 1, wherein said establishing means includes a foot bed for each of the feet of said individual and wherein at least one of said shim plates includes means for hingedly attaching said shim plate to said foot bed.

3. The apparatus of claim 2, wherein said foot shim is wedge shaped and wherein said shim plate is hingedly attached to said foot bed along the longitudinal centerline of said foot bed, whereby raising said shim plate to a predetermined angle defines the angle of said wedge shaped foot shim.

4. The apparatus of claim 2, wherein each foot bed carries four shim plates positioned respectively at the inner and outer positions of the foot of said individual at the heel and toe of said individual's foot.

5. The apparatus of claim 2, wherein said foot beds have an adjustable spacing therebetween.

6. The apparatus of claim 5 and further including lead screw means for adjusting the spacing between said foot beds.

7. The apparatus of claim 1, and further including means for ascertaining when a downward pressure applied to an outstretched elbow of an individual standing on said foot beds is at a predetermined level.

8. The apparatus of claim 7, wherein said pressure ascertaining means includes a load cell underneath one of said foot beds.

9. The apparatus of claim 8, wherein said pressure ascertaining means includes a threshold detector coupled to the output of said load cell and indicator means coupled to said threshold detector for indicating when said predetermined level has been reached.

10. A method for improving the athletic performance of an individual comprising the steps of positioning said individual on a pair of spaced apart foot beds, each of said foot beds having at least one positionable shim plate;
    adjusting said shim plate to a predetermined position;
    applying a predetermined pressure on the outstretched elbow of the individual over the foot having the adjusted shim plate while instructing the individual to resist the pressure;
    querying the individual as to the amount of effort acquired to keep the individual's elbow horizontal;
    readjusting the position of said shim plate and again querying the individual as to the amount of effort required to keep the individual's elbow horizontal;
    repeating the above steps to ascertain what shim position results in a reported least effort to keep the elbow horizontal, thus to establish an optimal shim position;
    configuring a foot shim to correspond to said optimal shim position; and, inserting said foot shim into said individual's shoe.

* * * * *